United States Patent [19]

Stec et al.

[11] Patent Number: 5,646,267
[45] Date of Patent: Jul. 8, 1997

[54] METHOD OF MAKING OLIGONUCLEOTIDES AND OLIGONUCLEOTIDE ANALOGS USING PHOSPHOLANES AND ENANTIOMERICALLY RESOLVED PHOSPHOLANE ANALOGUES

[75] Inventors: Wojciech J. Stec; Andrzej Grajkowski; Bogdan Uznanski, all of Lodz, Poland

[73] Assignee: Polish Academy of Sciences, Lodz, Poland

[21] Appl. No.: 462,418

[22] Filed: Jun. 5, 1995

Related U.S. Application Data

[60] Continuation of Ser. No. 108,878, Aug. 18, 1993, abandoned, which is a division of Ser. No. 883,622, May 12, 1992, Pat. No. 5,359,052, which is a continuation-in-part of Ser. No. 826,929, Jan. 23, 1992, abandoned, which is a continuation-in-part of Ser. No. 740,435, Aug. 5, 1991, abandoned.

[51] Int. Cl.$^6$ .................... C07H 21/02; C07H 21/04
[52] U.S. Cl. ............. 536/25.33; 536/25.1; 536/25.2; 536/25.3; 536/23.1
[58] Field of Search ................ 536/25.33, 25.1, 536/25.2, 25.3, 23.1

[56] References Cited

U.S. PATENT DOCUMENTS

| | | | |
|---|---|---|---|
| 3,687,808 | 8/1972 | Merigan et al. | 536/25.1 |
| 3,846,402 | 11/1974 | Eckstein et al. | 536/23.1 |
| 4,647,529 | 3/1987 | Rodland et al. | 435/6 |
| 4,806,463 | 2/1989 | Goodchild et al. | 435/5 |
| 5,112,963 | 5/1992 | Pieles et al. | 536/24.5 |
| 5,135,917 | 8/1992 | Burch | 514/44 |
| 5,194,428 | 3/1993 | Agrawal et al. | 514/44 |
| 5,212,295 | 5/1993 | Cook | 536/26.7 |
| 5,248,670 | 9/1993 | Draper et al. | 514/44 |
| 5,264,423 | 11/1993 | Cohen et al. | 514/44 |
| 5,271,941 | 12/1993 | Cho-Chung | 424/450 |
| 5,276,019 | 1/1994 | Cohen et al. | 514/44 |
| 5,334,711 | 8/1994 | Sproat et al. | 536/24.5 |
| 5,521,302 | 5/1996 | Cook | 536/25.31 |

FOREIGN PATENT DOCUMENTS

| | | |
|---|---|---|
| 0386563 | 9/1990 | European Pat. Off. . |
| 9308296 | 4/1993 | WIPO . |

OTHER PUBLICATIONS

Cosstick et al.(I), "An Approach to the Stereoselective Synthesis of Sp–dinucleoside Phosphorothioates Using Phosphotriester Chemistry," *Nucleic Acids Res.*, 15(23), 9921–9932 (1987).

Slim et al., "Conformationally Defined Phosphorothioate–Containing Oligoribonucleotides in the Study of the Mechanism of Cleavage of Hammerhead Ribozymes," *Nucleic Acids Res.*, 19(6), 1183–1188 (1991).

Stec et al.(I), "Reverse–Phase High–Performance Liquid Chromatographic Separation of Diastereomeric Phosphorothioate Analogues of Oligodeoxyribonucleotides and Other Backbone–Modified Congeners of DNA," *J. Chromatography*, 326, 263–280 (1985).

Stec et al.(II), "Novel Route to Oligo(Deoxyribonucleoside Phosphorothioates), Stereocontrolled Synthesis of P–Chiral Oligo(Deoxyribonucleoside Phosphorothioates)," *Nucleic Acids Res.*, 19(21), 5883–5888 (1991).

Stec et al.(III), "Automated Solid–Phase Synthesis, Separation, and Stereochemistry of Phosphorothioate Analogues of Oligodeoxyribonucleotides," *J. Am. Chem. Soc.*, 106(20), 6077–6079 (1984).

Stec et al.(IV), "Solid–Phase Synthesis, Separation, and Stereochemical Aspects of P–Chiral Methane– and 4,4'–Dimethoxytriphenylmethanephosphonate Analogues of Oligodeoxyribonucleotides," *J. Org. Chem.*, 50, 3905–3913 (1985).

Stec et al.(V), "Synthesis, Separation, and Stereochemistry of Diastereoisomeric Oligodeoxyribonucleotides Having a 5'–Terminal Internucleotide Phosphorothioate Linkage," *Tetrahedron Lett.*, 25(46), 5275–5278 (1984).

Lesnikowski et al.(I), "Stereoselective Synthesis of P–Homochiral Oligo(thymidine Methanephosphonates)," *Nucleic Acids Res.*, 16(24), 11675–11689 (1988).

Lesnikowski et al.(II), "Octa(thymidine methanephosphonates) of Partially Defined Stereochemistry: Synthesis and Effect of Chirality at Phosphorus on Binding to Pentadecadeoxyriboadenylic Acid," *Nucleic Acids Res.*, 18(8), 2109–2115 (1990).

Lesnikowski et al.(III), "Studies on Stereospecific Formation of P–Chiral Internucleotide Linkage. Synthesis of (Rp,Rp)– and (Sp,Sp)– thymidylyl(3',5')thymidine di(0,0)–phosphorothioate) Using a 2–Nitrobenzyl Group as a New S–Protection," *Tetrahedron Lett.*, 30(29), 3821–3824 (1989).

Lesnikowski et al.(IV), "Studies on Stereospecific Formation of P–Chiral Internucleotide Linkage. Synthesis of Diastereoisomeric 2'–Deoxyadenylyl(3',5') 2'–Deoxyadenylyl–S–Methylphosphorthioates via Nucleoside Hydroxyl Activation," *Tetrahedron*, 42(18), 5025–5034 (1986).

Cosstick et al.(II), "Synthesis of d(GC) and d(CG) Octamers Containing Alternating Phosphorothioate Linkages: Effect of the Phosphorothioate Group on the B–Z Transition, " *Biochemistry*, 24(14), 3630–3638 (1985).

(List continued on next page.)

*Primary Examiner*—John Kight
*Assistant Examiner*—L. Eric Crane
*Attorney, Agent, or Firm*—Stephen C. Macevicz

[57] ABSTRACT

Methods and compounds are provided for solid phase synthesis of oligonucleotides and related polymers by condensing protected monomer-O-[1,3,2-dichalcogen-substituted-phospholane] synthons in the presence of a catalytic base. Compounds of the invention include 2-N-substituted-1,3,2-dichalcogen-substituted-phospholane precursors of the above synthons, the protected monomer-O-[1,3,2-dichalcogen-substituted-phospholane] synthons, and P-chiral oligonucleotides and related P-chiral polymers.

7 Claims, No Drawings

OTHER PUBLICATIONS

Eckstein(I), "Nucleoside Phosphorothioates," *Ann. Rev. Biochem.*, 54, 367–402 (1985).

Eckstein(II), "Phosphorothioate Analogues of Nucleotides—Tools for the Investigation of Biochemical Processes," *Angew. Chem. Intl. Ed.*, 22(6), 423–506 (1983).

Eckstein(III), "Stabilization of DNA by Incorporation of Phosphorothioate Groups," *Nucleosides & Nucleotides*, 4(1 & 2), 77–79 (1985).

Eckstein et al.(I), "Polyribonucleotides Containing a Phosphorothioate Backbone," *Eur. J. Biochem.*, 13(3), 558–564 (1970).

Eckstein et al.(II), "Phosphorothioates in Molecular Biology," *Trends in Biochemical Science*, 14, 97–100 (1989).

Connolly et al.(I), "The Stereochemical Course of the Restriction Endonuclease *EcoRI*–catalyzed Reaction," *J. Biological Chem.*, 259(17), 10760–10763 (1984).

Connolly et al.(II), "Synthesis and Characterization of an Octanucleotide Containing the *EcoRI* Recognition Sequence with a Phosphorothioate Group and the Cleavage Site," *Biochemistry*, 23(15) 3443–3453 (1984).

De Clercq et al., "Interferon Induction Increased through Chemical Modification of a Synthetic Polyribonucleotide," *Sciece*, 165, 1137–113 (1969).

Ott et al., "Protection of Oligonucleotide Primers against Degradation by DNA Polymerase I," *Biochemistry*, 26(25), 8237–8241 (1987).

Potter et al., "A Stereospecifically $^{18}$O–labelled Deoxydinucleoside Phosphate Block for Incorporation into an Oligonucleotide," *Nucleic Acids Res.*, 11(20), 7087–7103 (1983).

Spitzer et al., "Inhibition of Deoxyribonucleases by Phosphorothioate Groups in Oligodeoxyribonucleotides," *Nucleic Acids Res.*, 16(24), 11691–11704 (1988).

Matzura et al., "A Polyriboncleotide Containing Alternating –>P=O and –>P=S Linkages," *Eur. J. Biochem.*, 3(4), 448–452 (1968).

Cruse et al., "Chiral Phosphorothioate Analogues of β–DNA. The Crystal Structure of Rp–dIGp(S)CpGp(S)CpGp(s)Cl," *J. Mol. Biol.*, 192, 891–905 (1986).

LaPlanche et al., "Phosphorothioate Modified Oligodeoxyribonucleotides. III. NMR and UV Spectroscopic Studies of the Rp–Rp, Sp–Sp, and Rp–Sp Duplexes, [d(GG$_3$AATTCC)]$_2$, Derived for Diastereomeric O–Ethyl Phosphorothioates," *Nucleic Acids Res.*, 14(22), 9081–9093 (1986).

Fujii et al., "Acylphosphonates. 7. A New Method for Stereospecific and Stereoselective Generation of Dideoxyribofuranoside Phosphorothioates Via the Acylphosphonate Intermediates," *Tetrahedron*, 43(15), 3395–3407 (1987).

Gallo et al., "Alkyl Phosphotriester Modified Oligodeoxyribonucletides. V. Synthesis and Absolute Configuraion of Rp and Sp Diastereomers of an Ethyl Phosphotriester (Et) Modified *EcoRI* Recognition Sequence, d[GGAA-(Et)TTCC]. A Synthetic Approach to Regio– and Stereospecific Ethylation–Interference Studies," *Nucleic Acids Res.*, 14(18), 7405–7420 (1986).

Nelson et al., "Synthesis of P–Thioadenylyl–(2'–5')–adenosine and P–Thioadenylyl–(2'–5')–P–Thioadenylyl–(2'–5')–adenosine," *J. Org. Chem.*, 49(13), 2314–2317 (1984).

Brody et al., "Unambiguous Determination of the Stereochemistry of Nucleotidyl Transfer Catalyzed by DNA Polymerase I from *Escherichia coli*," *Biochemistry*, 20(5), 1245–1252 (1981).

Marugg et al., "Synthesis of Phosphorothioate–Containing DNA Fragments by a Modified Hydroxybenzotriazole Phosphotriester Approach," *Nucleic Acids Res.*, 12(23), 9095–9110 (1984).

Zon, "Oligonucleotide Analogues as Potential Chemotherapeutic Agents," *Pharmaceutical Research*, 5(9), 539–549 (1988).

Cook, U.S. Patent Application 07/463,358, filed Jan. 11, 1990.

Cook, U.S. Patent Application 07/566,977, filed Aug. 13, 1990.

METHOD OF MAKING OLIGONUCLEOTIDES AND OLIGONUCLEOTIDE ANALOGS USING PHOSPHOLANES AND ENANTIOMERICALLY RESOLVED PHOSPHOLANE ANALOGUES

CROSS REFERENCE TO RELATED APPLICATIONS

This application is a continuation of U.S. application Ser. No. 08/108,878, filed Aug. 19, 1993, now abandoned which is a division of U.S. application Ser. No. 07/883,622, now U.S. Pat. No. 5,359,052, filed May 12, 1992, which is a continuation-in-part of U.S. application Ser. No. 07/826,929, filed Jan. 23, 1992, now abandoned which is a continuation-in-part of U.S. application Ser. No. 07/740,435, filed Aug. 5, 1991, which is now abandoned.

FIELD OF THE INVENTION

The invention relates generally to the solid phase synthesis of oligonucleotides, and more particularly, to methods and compounds for synthesizing P-chiral oligonucleotide analogs.

BACKGROUND

The development of reliable and convenient methods for solid phase synthesis of polynucleotides has led to many advances in molecular biology and related fields, e.g. Itakura, Science, Vol. 209, pgs. 1401–1405 (1980); Caruthers, Science, Vol. 230, pgs 281–285 (1985); and Eckstein, ed., Oligonucleotides and Analogues: A Practical Approach (IRL Press, Oxford, 1991). In particular, the availability of synthetic oligonucleotides and a variety of nuclease-resistant analogs, e.g. phosphorothioates, methylphosphonates, and the like, has encouraged investigation into their use as therapeutic compounds for treating a variety of conditions associated with the inappropriate expression of indigenous and/or exogenous genes, e.g. Cohen, Ed., Oligonucleotides: Antisense Inhibitors of Gene Expression (Macmillan Press, New York, 1989); Van der Krol et al, Biotechniques, Vol. 6, 958–976 (1988); Matsukura et al, Proc. Natl. Acad. Sci., Vol. 86, pgs. 4244–4248 (1989); Iyer et al, Nucleic Acids Research, Vol. 18, pgs. 2855–2859 (1990); Leiter et al Proc. Natl. Acad. Sci, Vol. 87, pgs. 3430–3434 (1990); McManaway et al, Lancet, Vol. 335, pgs. 808–811 (1990); Manson et al, Lymphokine Research, Vol. 9, pgs. 35–42 (1990); Sankar et al, Eur. J. Biochem., Vol. 184, pgs. 39–45 (1989); Agrawal et al, Proc. Natl. Acad. Sci., Vol. 86, pgs. 7790–7794 (1989); Miller, Biotechnology, Vol. 9, pgs. 358–362 (1991); Chiang et al, J. Biol. Chem., Vol. 266, pgs. 18162–18171 (1991); Calabretta, Cancer Research, Vol. 51, pgs. 4505–4510 (1991), and the like. Usually, these compounds are employed as "antisense" compounds. That is, the compounds are oligonucleotides, or analogs thereof, that have a base sequences complementary to segments of target nucleic acids, usually RNAs, such that duplexes or triplexes form that either render the respective targets more susceptible to enzymatic degradation, block translation or processing, or otherwise block or inhibit expression, e.g. Cohen (cited above); Moser et al, Science, Vol. 238, pgs. 645–650 (1987).

Many of the phosphate-analog linkages of these antisense compounds, as well as those of related non-nucleosidic polymers, are chiral at the phosphorus, e.g. phosphorothioates, phosphoroselenoates, methylphosphonates, and the like, Zon, Pharmaceutical Research, Vol. 5, pgs. 539–549 (1988); and Uhlmann and Peyman, Chemical Reviews, Vol. 90, pgs. 543–584 (1990). Currently, there is no way to control the chirality of these phosphorus linkages during solid phase synthesis. Consequently, the synthesis of such polymers results in mixtures of diastereoisomers, wherein the individual polymers of the mixtures have random sequences of $R_p$ and $S_p$ chiral phosphorus linkages along their backbones. Such mixtures prepared by currently available technology consist of $2^n$ diastereoisomers, where n is the number of P-chiral linkages in the polymer. For example, a trimer with two P-chiral linkages has $2^2=4$ possible diastereoisomers, indicated by the following 5'→3' sequences of linkages: $R_p$—$R_p$, $R_p$—$S_p$, $S_p$—$R_p$, and $S_p$—$S_p$. In addition to the lack of methods for synthesizing polymers of predetermined chirality, there is also a lack of available analytical tools for direct measurement of the reproducibility of preparing a diastereoisomer population of polymers having P-chiral linkages for anything greater than 4-mere, Zon, pgs. 301–349 in Hancock, Ed., High-Performance Liquid Chromatography in Biotechnology (John Wiley, New York, 1990). The inability to prepare oligonucleotide analogs and related non-nucleosidic polymers with predetermined sequence, length, and chirality is problematic because there is strong evidence that chirality is an important factor in duplex stability and nuclease resistance, e.g. Lesnikowski et al, Nucleic Acids Research, Vol. 18, pgs. 2109–2115 (1990); Burgers et al, J. Biol. Chem., Vol. 254, pgs. 7476–7478 (1979); Miller et al, Biochem., Vol. 18, pgs. 5134–5143 (1979); Zon, Pharmaceutical Research (cited above); Eckstein, Ann. Rev. Biochem., Vol. 54, pgs. 367–402 (1985); and the like. This evidence suggests that stereo-controlled synthesis of antisense and related compounds with predetermined chirality at each P-stereogenic center might allow one to design particular therapeutic diastereoisomers which form maximally stable duplexes and which are maximally resistant towards nucleolytic enzymes, thus increasing their effective life times, and in this way decreasing the required amount of xenobiotic material for a given therapeutic effect.

SUMMARY OF THE INVENTION

The invention is directed to a new method of synthesizing oligonucleotides and related polymers whose monomeric units are linked by phosphate groups, or analogs thereof. In a preferred embodiment of the invention, the method includes synthesis of such compounds with predetermined chirality whenever the phosphorus linkages are chiral. The invention includes synthons and synthon precursors for making such polymers, as well as the polymers themselves whenever the phosphorus linkages are chiral and their sequence of chirality predetermined. The synthons of the invention are hydroxyl-protected monomer-O-[1,3,2-dichalcogen-substituted-phospholane]s which may be separated into their $R_p$ and $S_p$ chiral forms, where appropriate, to permit solid phase synthesis of a polymer having a predetermined sequence of $R_p$ or $S_p$ linkages.

The method of the invention comprises the following steps: (a) providing a first monomer attached to a solid phase support, the first monomer having a protected hydroxyl; (b) deprotecting the protected hydroxyl to form a free hydroxyl; (c) reacting with the free hydroxyl in the presence of a catalytic base a synthon selected from Formula I (below); and (d) repeating steps (b) and (c) until a polymer of predetermined length is obtained. Preferably, the method further comprises the step of capping unreacted hydroxyl groups after the step of reacting. An important feature of the method of the invention is to attach the first monomer to a solid phase support by a linking group which is not cleaved in the presence of the catalytic base.

Preferably, whenever a P-chiral linkage is formed between monomers, step (d) comprises repeating steps (b) and (c) until a polymer of predetermined length and chirality is obtained. Most preferably, whenever a P-chiral linkage is formed between monomers and the monomers are nucleosides or analogs thereof, step (c) includes selecting the desired P-chiral form of the synthon of Formula I and step (d) comprises repeating steps (b) and (c) until a P-chiral oligonucleotide of predetermined length is obtained.

The present invention provides a new chemistry for synthesizing oligonucleotides and related polymers having phosphate, or phosphate analog, linkages. In particular, whenever the phosphate analog linkages are P-chiral, the present invention provides a method of synthesizing polymers having a predetermined sequence of P-chirality along the polymer backbone. P-chiral oligonucleotides of the invention can be employed as antiviral agents, antisense therapeutic compounds, hybridization probes, and the like.

DETAILED DESCRIPTION OF THE INVENTION

The invention provides a novel approach to solid phase synthesis of oligonucleotides and related polymers using hydroxyl-protected monomer-O-[1,3,2-dichalcogen-substituted-phospholane] synthons. In particular, the invention includes 2-N-substituted-1,3,2-dichalcogen-substituted-phospholane precursors of the above synthons, the hydroxyl-protected monomer-O-[1,3,2-dichalcogen-substituted-phospholane] synthons themselves, and P-chiral oligonucleotides and related P-chiral polymers having lengths in the range of 4 to several hundred monomers, and preferably, in the range of 12 to 60 monomers.

Polymers synthesized by the method of the invention generally have the formula:

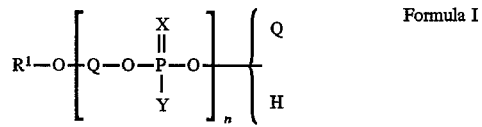

Formula I wherein: Q is an alkyl or alkenyl having from 1 to 8 carbon atoms; an alkyloxy or alkylthio having from 1 to 8 carbon atoms and from 1 to 2 oxygen or sulfur heteroatoms; or when taken together with both adjacent oxygens, is a nucleoside or a nucleoside analog. Preferably, Q is alkyl or alkenyl having from 3 to 6 carbon atoms, or alkoxy having from 3 to 6 carbon atoms and one oxygen atom, or when taken together with both adjacent oxygens, is a nucleoside or a nucleoside analog. More preferably, Q is alkyl having from 3 to 6 carbon atoms, or a cyclic alkoxy having from 4 to 5 carbon atoms and one oxygen atom, or when taken together with both adjacent oxygens, is a nucleoside or a nucleoside analog. $R^1$ is hydrogen or a hydroxyl protecting group, such as triphenylmethyl (i.e., trityl), p-anisyldiphenylmethyl (i.e., monomethoxytrityl or MMT), di-p-anisylphenylmethyl (i.e., dimethoxytrityl or DMT), pivaloyl acetyl 4-methoxytetrahydropyran-4-yl, tetrahydropyranyl, phenoxyacetyl, isobutyloxycarbonyl, pixyl, benzyl, trialkylsilyl having from 3 to 9 carbon atoms, 9-fluorenylmethyl carbamate (Fmoc), or the like. Greene and Wuts, Protective Groups in Organic Synthesis, 2nd Edition (John Wiley, New York, 1991) provides extensive guidance on the selection of protecting groups for the various embodiments of the invention.

X is chalcogen, preferably S, O or Se, or a substituted imino of the form $=NR^2$ wherein $R^2$ is alkyl having from 1 to 6 carbon atoms or $R^2$ is aryl, alkyl-substituted aryl, or alkenyl-substituted aryl having from 6 to 12 carbon atoms. Y is chalcogen, preferably S, O, or Se. n is in the range of 1 to several hundred. Preferably, n is in the range of 5–200; more preferably, n is in the range 12–60; and most preferably, n is in the range of 15–30.

The synthons of the invention are hydroxyl-protected monomer-O-[1,3,2-dichalcogen-substituted-phospholane]s, preferably defined by the formula:

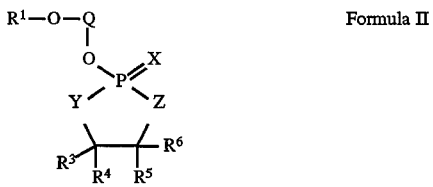

Formula II $Q$, $R^1$, X, and Y are defined as above. Z is S or Se; and more preferably, Z is S. $R^3$, $R^4$, $R^5$, and $R^6$ are separately hydrogen or an electron-withdrawing group. Preferably, $R^3$, $R^4$, $R^5$, and $R^6$ are separately alkyl having from 1 to 4 carbon atoms, or are separately or together with the carbon atoms to which they are attached aryl or alkyl-substituted aryl having from 6 to 12 carbon atoms. Whenever a particular selection of $R^3$, $R^4$, $R^5$, and $R^6$ result in chirality, it is understood that the synthon of Formula II is used with a given stereochemical array of these ring substituents. The synthon of formula II is made by reacting the following cyclic phosphite with a free hydroxyl of an appropriate monomer:

Formula III wherein Y, Z, and $R^3$ through $R^6$ are defined as above, and W is a leaving group amenable to nucleophilic attack by a free hydroxyl of a monomer. Preferably, W is halogen, dialkylamino having from 2 to 6 carbon atoms, morpholinyl, piperidinyl, or pyrrolidinyl. More preferably, W is selected from the group consisting of Cl, morpholino, and diisopropylamino.

P-chiral polymers of the invention are generally defined by Formula I, with the provisos that X and Y are not the same in at least one linkage and that not all linkages in the same polymer need be identical. More particularly, P-chiral oligonucleotides of the invention are defined by the formula:

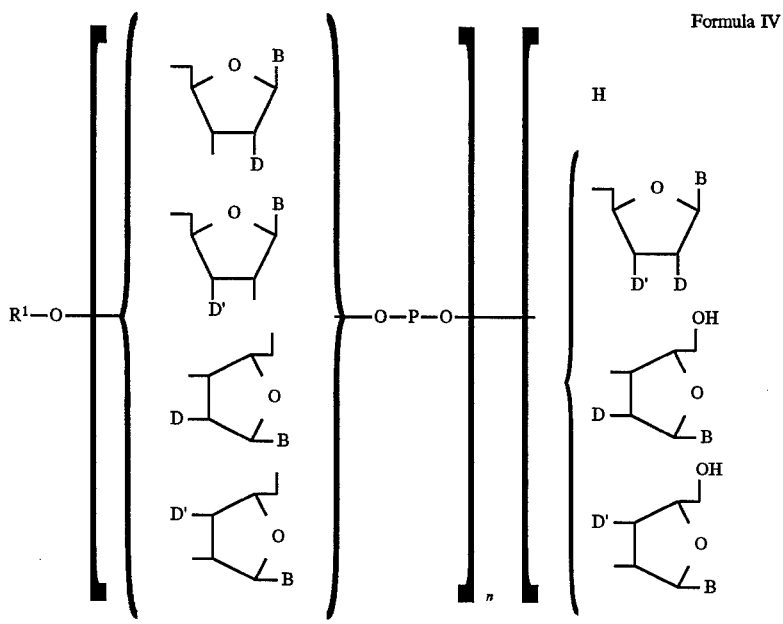

Formula IV wherein X, Y, and R¹ are defined as above, again with the proviso that X and Y are not the same in at least one linkage and that not all linkages in the same oligonucleotide need be identical. B is a natural or synthetically modified purine or pyrimidine base. D' is a 3'-hydroxyl protecting group. D is hydrogen halogen, hydroxyl, or —OR', wherein R' is alkyl having from 1 to 3 carbon atoms or a 2'-hydroxyl protecting group, such as alkylsilyl, e.g. t-butyldimethylsilyl, or the like. Preferably, n is in the range of 5–200, and more preferably in the range of 12–60. It is understood from Formula IV that P-chiral oligonucleotides of the invention may include 5'-3', 5'-2', 5'-5', 3'-3', 2'-2', and 3'-2' linkages between nucleosides by the appropiate selection of synthons of Formula II.

The term "oligonucleotide" as used herein includes linear oligomers of natural or modified nucleosides, including deoxyribonucleosides, ribonucleosides, α-anomeric forms thereof, and the like, usually linked by phosphodiester bonds or analogs thereof ranging in size from a few monomeric units, e.g. 3–4, to several hundreds of monomeric units. Preferably, oligonucleotides of the invention are oligomers of the natural nucleosides having a lengths in the range of 12 to 60 monomeric units, and more preferably, having lengths in the range of 15 to 30 monomeric units. Whenever an oligonucleotide is represented by a sequence of letters, such as "ATGCCTG," it will be understood that the nucleotides are in 5'→3' order from left to right.

Phosphorus linkages between nucleosidic monomers include phosphodiester bonds and analogs of phosphodiester bonds, such as phosphorothioate, phosphorodithioate, phosphoroselenoate, phosphorodiselenoate, phosphoroanilothioate, phosphoranilidate, and the like. Preferably, the monomers of the oligonucleotides of the invention are linked by phosphodiester, phosphorothioate, or phosphorodithioate linkages.

As used herein, "nucleoside" includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described generally by Scheit, Nucleotide Analogs (John Wiley, New York, 1980). Such analogs include the natural and synthetic nucleosides with or without appropriate protecting groups for synthesis in accordance with the invention. An exemplary list of nucleoside analogs includes 2-aminopurine, deoxyinosine, $N^4$-methoxydeoxycytidine, $N^4$-aminodeoxycytidine, 5-fluorodeoxyuridine, and the like.

The term "electron-withdrawing" denotes the tendency of a substituent to attract valence electrons of the molecule of which it is apart, i.e. it is electronegative, March, Advanced Organic Chemistry, pgs. 16–18 (John Wiley, New York, 1985).

Some aspects of the invention are common to other approaches to solid phase synthesis of oligonucleotides, e.g. selection of protecting groups, selection of solid phase supports, and the like. Consequently, considerable guidance in making such selections in the context of the present invention can be found in literature, e.g. Gait, editor, Oligonucleotide Synthesis: A Practical Approach (IRL Press, Oxford, 1984); Amarnath and Broom, Chemical Reviews, Vol. 77, pgs. 183–217 (1977); Pen et al, Biotechniques, Vol. 6, pgs. 768–775 (1988); Ohtsuka et al. Nucleic Acids Research, Vol. 10, pgs. 6553–6570 (1982); Eckstein, editor (cited above), Greene and Wuts (cited above), Narang, editor, Synthesis and Applications of DNA and RNA (Academic Press, New York, 1987), and the like.

Synthon precursors of the invention are generally synthesized in accordance with the following scheme:

Scheme I

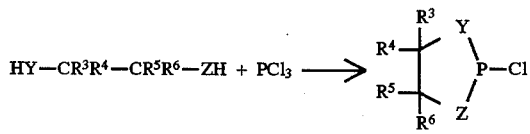

Generally, the synthon precursors are synthesized by reacting an appropriately 1,2-substituted ethane derivative with phosphorus trichloride in an aprotic solvent, preferably hexane, diethyl ether, or methylene chloride, at a temperature in the range of 10°–30° C., in the presence of a base, such as, trialkylamine or pyridine. Preferably, the base employed is pyridine. The resulting 2-chloro-1,3,2-dichalcophospholane is then reacted with secondary amines, such as N,N-diisopropylamine or morpholine, to give the preferred synthon precursors.

Synthons of the invention are generally synthesized in accordance with the following scheme:

Scheme II

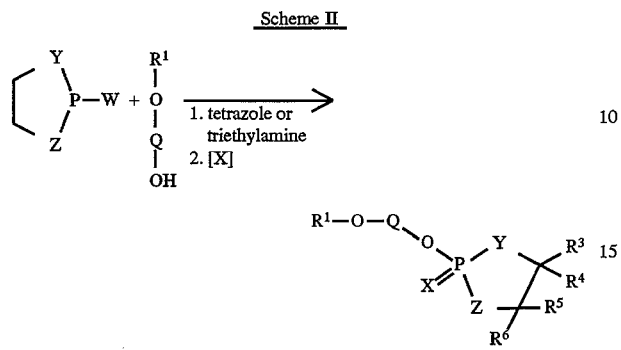

wherein $R^1$, $R^3$ through $R^6$, W, X, Q, Y, and Z are defined as above. [X] represents an agent for transferring the X moiety to the phosphorus. When X is O, [X] is elemental oxygen, t-butyl hydroxide, or a peroxide, e.g. hydrogen peroxide, methyl hydroperoxide, ethyl hydroperoxide, diethyl peroxide, or the like. When X is S, [X] is elemental sulfur, 1,1-dioxo-3H-1,2-benzodithiol-3-one, or an acyl disulfide or corresponding diphosphorothioyl disulfide, e.g. Stec et al, PCT/US91/01010. When X is Se, [X] is elemental selenium or a saturated solution of potassium selenocyanate, e.g. in 95% pyridine/5% triethylamine as taught by Stec et al, J. Amer. Chem. Soc., Vol. 106, pgs. 6077–6079 (1984). When X is $NR^2$, [X] is azide of the form $N_3R^2$, wherein $R^2$ is aryl having from 6 to 12 carbon atoms. Preferably, $R^2$ is phenyl. Preferably, the reaction is carried out in an aprotic organic solvent, e.g. methylene chloride, or like solvent, and when W is non-halogen, is catalyzed with a mild acid, such as tetrazole or substituted tetrazole, e.g. Dahl et al, Nucleic Acids Research, Vol. 15, pgs. 1729–1743 (1987). When W is halogen, the reaction is preferably catalyzed by a mild base, such as pyridine, substituted pyridine, or trialkylamine. Preferably, the mild base is triethylamine or diisopropylethylamine.

Whenever Q, X, Y, and Z are selected so that the synthon is P-chiral, the $R_p$ and $S_p$ forms of the synthon must be separated prior to synthesizing polymers of predetermined chirality at the P-stereogenic centers. As used herein, "$R_p$" and "$S_p$" refer to the alternative stereo-configurations of the chiral phosphorus atoms in either the synthons or the phosphorus linkages in the polymers. Exemplary $R_p$ and $S_p$ dimers are shown below:

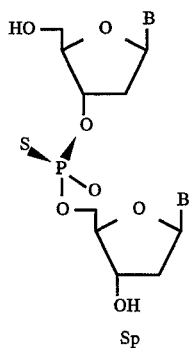

Sp

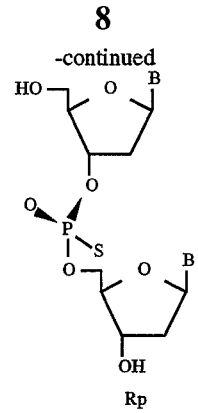

Rp

In reference to P-chiral polymers, the sequence of chiral phosphorus atoms is denoted by subscripts "ps" or "pr" between monomers, e.g. $Q_{ps}Q_{ps}Q_{ps}Q_{ps}Q$ for a pentamer having four $S_p$ phosphorus linkages, or $A_{ps}T_{pr}G_{ps}A_{pr}C_{ps}T_{pr}T_{ps}G_{pr}G_{ps}A_{pr}C$ for an 11-mer oligonucleotide having alternating $R_s$ and $R_p$ phosphorus linkages (where A, C, G, and T represent the natural 2'-deoxynucleosides deoxyadenosine, deoxycytidine, deoxyguanosine, and deoxythymidine, respectively, unless otherwise specified). When the phosphorus linkage is achiral, no designation will be made between monomers. Thus, $Q_{ps}QQQQ$ represents a pentamer with a single P-chiral linkage of the $S_p$ type, while the rest of the linkages are either achiral or of mixed $R_p$ and $S_p$ chirality.

In regard to nucleoside monomers, the phospholane moiety of the synthons can be attached to either the 3' or 5' hydroxyl, permitting either 3'→5' or 5'→3' synthesis of oligonucleotides. Preferably, the phospholane moiety is attached via the 3' hydroxyl.

Separation of the $R_p$ and $S_p$ chiral forms of the synthons is carried out using standard techniques, usually silica gel chromatography or high performance liquid chromatography (HPLC), e.g. Mislow, Introduction to Stereochemistry (W. A. Benjamin, New York, 1966). In regard to nucleoside synthons, in some cases the $R_p$ and $S_p$ forms can be identified by differential susceptibility to digestion of their oligomers to well known nucleases, but usually the $R_p$ form is the slower eluting diastereoisomer under HPLC conditions described below. Conventional X-ray crystallography and 2-D NMR methods can also be used to assign the absolute stereochemistry at phosphorus in cases where the chirality of the monomer is known. As used herein, "diastereoisomerically pure" in reference to the $R_p$ and $S_p$ forms of the synthons of the invention or in reference to oligomers with a particular sequence or $R_p$ and $S_p$ chirality means the indicated stereochemistry essentially free of all other phosphorus configurations. Preferably, it means a compound consisting of greater than 95% of the indicated stereochemistry for each linkage, an a molar basis, and less than 5% of other phosphorus configurations for each linkage. More preferably, it means a compound consisting of greater than 99% of the indicated stereochemistry far each linkage, on a major basis, and less than 1% of other phosphorus configurations for each linkage.

Polymers of the inventions are generally synthesized in accordance with the following scheme:

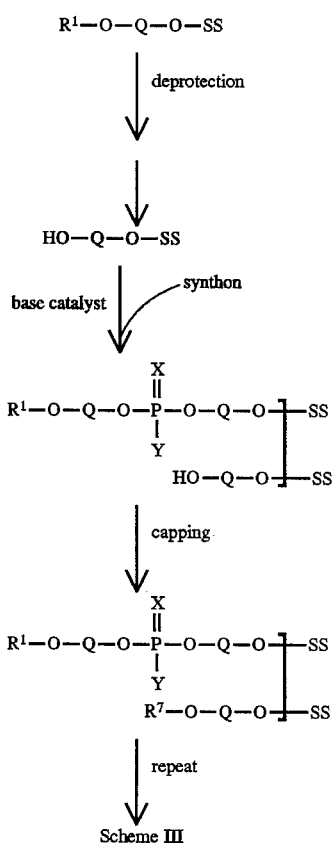

Scheme III wherein Q, X, Y, and Z are defined as above, and wherein SS is a solid phase support and $R^7$ is a capping agent, e.g. acyl, isopropylphosphonate, or the like. An important feature of the coupling reaction is the presence of a catalytic base, preferably non-nucleophilic, such as potassium tert-butanolate, 1-methylimidazole, N-methylimidazole, 4-dimethylaminopyridine (DMAP), 1,8-diazabicyclo[5.4.0] undec-7-ene (DBU), or the like. Preferably, DBU is employed as the catalytic base, and is employed in large (e.g. about 100–300×) molar excess of the reactants. The coupling reaction can be performed in an anhydrous organic solvent, such as acetonitrile, methylene chloride, N,N-dimethylformamide, or the like. It is understood that SS may include a solid phase support with oligonucleotides attached that have been synthesized using a different chemistry, e.g. employing phosphoramidite synthons.

A variety of solid phase supports can be used with the present invention, but controlled pore glass or polystyrene are preferred. Preferably, the solid phase support is derivatized with the first monomer of the polymer chain to be synthesized, such that the linking group connecting the monomer to the support is stable in the presence of the catalytic base and other reagents employed in the synthesis cycle. Preferably, polymers of the invention are attached to solid phase supports, e.g. controlled pore glass (CPG), by a sarcosinyl linker, as taught by Brown et al, J. Chem. Soc. Chem. Commun., 1989, pgs. 891–893; and Pfleiderer et al, Tetrahedron Letters, Vol. 31, pg. 2549 (1990). Briefly, the solid phase support is functionalizod as follows: 9-fluorenylmethoxycarbonyl-sarcosine (FMOC-sarcosine) (10 equiv.) and dicyclohexylcarbodiimide (DCC)(15 equiv.) are added to long chain alkylamino-CPG in a mixture of N,N-dimethylformamide (DMF) and dichloromethane. Removal of the FMOC group with piperidine in pyridine is followed by coupling of the sarcosine methylamino group to a hydroxyl-protected-monomer-O-succinate (10 equiv.) in the presence of DCC (15 equiv.). For 5'-O-DMT-protected nucleosides, this results in a loading of about 20 microquiv. per gram of dry support.

Preferably, in addition to the general steps of the synthesis cycle given above, after each coupling step, a capping step is added wherein unreacted free hydroxyls are reacted with a group that prevents further monomer addition. Preferably, the unreacted free hydroxyls are reacted with capping solution consisting of one part acetic anhydride/lutidine in tetrahydrofuran (THF) (10:10:80 v/v/v) and one part N-methylimidazole in THF (16:84 v/v). More preferably, the solid phase support is washed with a suitable solvent, usually acetonitrile, after each deprotection, coupling, and capping step.

Preferably, the method of the invention is automated. The apparatus for automating can take several forms. Generally, the apparatus comprises a series of reagent reservoirs, a synthesis chamber containing the solid phase support and a computer controlled means for transferring in a predetermined manner reagents from the reagent reservoirs to and from the synthesis chamber and the purification chamber, and from the synthesis chamber to the purification chamber. The computer controlled means for transferring reagents can be implemented by a general purpose laboratory robot, such as that disclosed by Wilson et al, BioTechniques, Vol. 6, pg. 779 (1988), or by a dedicated system of tubing, and electronically controlled valves. Preferably, the computer controlled means is implemented by a dedicated system of valves and tubing connecting the various reservoirs and chambers. In further preference, the reagents are driven through the tubing by maintaining a positive pressure in the reagent reservoirs by means of a pressurized inert gas, such as argon, as is used by many widely available automated synthesizers, e.g. Applied Biosystems, Inc. models 380B or 381A DNA synthesizers.

Oligonucleotides of the invention can be employed as hybridization probes, as taught in Hames et al, editors, Nucleic Acid Hybridization: A Practical Approach (IRL Press, Oxford, 1985).

Polymers of the invention can also be employed as components of pharmaceutical compositions. In the case of poly(alkyl or alkenyl phosphate)s of the invention, such compositions contain an antiviral therapeutic amount of at least one of the poly(alkyl or alkenyl phosphate) and/or at least one of their thiophosphate analogs in a pharmaceutically effective carrier. The poly(alkyl or alkenyl phosphate)s and their thio analogs may be administered either as a single chain length (i.e. one value of n), or as a defined mixture containing polymers of more than one chain length. Most preferably, a single chain length is employed in the range of 15 to 30 monomers.

A variety of diseases and disorders can be treated by administration of a composition comprising antisense oligonucleotides of the invention. Viral diseases that can be treated by antisense inhibition of nucleic acid expression include, but are not limited to, those caused by hepatitis B virus, cytomegalovirus, herpes simplex virus I or II, human immunodeficiency virus type I or II, influenza virus, respiratory syncytial virus, and human papilloma virus. Malignancies which can be treated by administration of antisense compounds of the invention include, but are not limited to, lung cancer (e.g., small cell lung carcinoma), colorectal cancer, prostate cancer, breast cancer, and leukemias and lymphomas. In such diseases, the antisense compounds are targeted to aberrantly expressed oncogenes associated with the diseases, or to other genes being inappropriately expressed as part of the disease condition, e.g. Aaronson, Science, Vol. 254, pgs. 1146–1153 (1991). Acute inflammatory and immune reactions, such as septic shock, eosinophilia, and the like, can also be treated with antisense compounds of the invention, wherein inappropriately and/or aberrantly expressed cytokine genes are inhibited, e.g. Tracey et al, Nature, Vol. 330, pgs. 662–664 (1987), U.S. Pat. No. 5,055,447, and Waage et al, J. Exp. Med. Vol. 169, pgs. 333–338 (1989)(antisense TNF-α and/or TNF-β); Starnes et al, J. Immunol., Vol. 145, pgs. 4185–4191 (1990), and Fong et al, J. Immunol., Vol. 142, pgs. 2321–2324 (antisense IL-6); Coffman et al, Science, Vol. 245 pgs. 308–310 (antisense IL-5); Finkelman et al, J. Immunol., Vol. 141, pgs. 2335–2341 (1988)(antisense IL-4); Young et al, Blood, Vol. 68, pgs. 1178–1181 (1986)(antisense GM-CSF); and the like.

A pharmaceutical carrier can be any compatible, nontoxic substance suitable for delivering the compositions of the invention to a patient. Sterile water, alcohol, fats, waxes, neutral lipids, cationic lipids, and inert solids may be included in a carrier. Pharmaceutically acceptable adjuvants, e.g. buffering agents, dispersing agents, and the like, may also be incorporated into the pharmaceutical composition. For topical administration, the compositions of the invention are formulated into ointments, salves, gels, or creams, as generally known in the art. Generally, compositions useful for parenteral administration of drugs are well known, e.g. Remington's Pharmaceutical Science, 15th ED. (Mack Publishing Company, Easton, Pa., 1980). Compositions of the invention may also be administered by way of an implantable or injectable drug delivery system, e.g. Urquhart et al, Ann. Rev. Pharmacol. Toxicol., Vol. 24, pgs. 199–236 (1984); Lewis, ed. Controlled Release of Pesticides and Pharmaceuticals (Plenum Press, New York, 1981); U.S. Pat. No. 3,773,919; U.S. Pat. No. 3,270,960; or the like. Compounds of the invention may also be conjugated to transport moieties to aid in targeting tissues or in penetrating cell membranes and the like, e.g. as taught by Latham et al, PCT application WO 91/14696.

Preferably, compositions of the invention are administered parenterally, and more preferably, intravenously. In such cases, pharmaceutical carriers include saline solutions, dextrose solutions, combinations of the two, nonaqueous solutions such as ethyl oleate, and the like.

Selecting an administration regimen for a composition of the invention depends on several factors, including the rate of degradation of the particular compounds in serum, the accessibility of the target tissues and cells, pharmacokinetics, toxicity, and the like. Preferably, an administration regimen maximizes the amount of compound delivered to a patient consistent with an acceptable level of side effects. Accordingly, the amount of compound delivered may depend on the particular compound and the severity of the viral infection or other condition being treated. Preferably, a daily dose of the compounds of the invention is in the range of about 1–2 µg/kg to about 10–20 mg/kg.

EXAMPLE 1

2-chloro-1,3,2-oxathiaphospholane

Into the mixture of pyridine (79.1 g, 1.0 mol) and benzene (400 mL) were added at room temperature, with stirring, 2-mercaptoethanol (39.1 g, 0.5 mol) and phosphorus trichloride (68.7 g, 0.5 mol). Stirring was continued for 0.5 h, pyridinium chloride was filtered off, and the filtrate was condensed under reduced pressure. Crude product was purified via distillation under reduced pressure, and the fraction boiling at 70°–72° C./20 mmHg, was collected. $^{31}$P NMR: δ205.0 ppm (benzene). Yield 72%.

EXAMPLE 2

N,N-diisopropvlamino-1,3,2-oxathiaphosholane

Into the solution of the 2-chloro-1,3,2-oxathiaphospholane of Example 1 (28.5 g, 0.2 mol) in n-pentane (300 mL) was added dropwise, at room temperature, with stirring, N,N-diisopropylamine (40.5 g, 0.4 mol). After 0.5 h diisopropylamine hydrochloride was removed by filtration, solvent was evaporated under reduced pressure, and the product was distilled. The fraction collected at 70° C./0.1 mmHg was shown by means of $^{31}$P NMR to be homogeneous. Yield: 70%. $^{31}$P NMR: β147.8 ppm (benzene). MS: m/z 207 (M⁻, E.I., 15 eV).

EXAMPLE 3

2-N,N-diisopropylamino-4,4-dimethyl-1,3,2-oxathiaphospholane

Into a solution of 20 mmoles of anhydrous pyridine in benzene (25 mL) was added at temperature of 0°–5°C., dropwise, with stirring, a mixture of 10 mmoles of 2-methyl-2-mercaptopropanol-1 and 10 mmoles of phosphorus trichloride. The reaction mixture was then maintained at ambient temperature for 1 h. Pyridine hydrochloride was filtered off and the filtrate was concentrated under reduced pressure. Distillation gave 2-chloro-4,4-dimethyl-1,3,2-oxathiaphospholane, b.p. 48°–52° C./0.1 mmHg. Ten mmoles of this compound were dissolved in 25 mL of n-hexane and to this solution 20 mmoles of N,N-diisopropylamine were added, with stirring, at room temperature. After 1 h diisopropylamine hydrochloride was removed by filtration and the product, 2-N,N-diisopropylamino-4,4-dimethyl-1,3,2-oxathiaphospholane, was distilled under reduced pressure. The fraction at 86°–90° C./0.1 mmHg, ⁻P NMR ($C_6D_6$) d154.3 ppm, was collected.

EXAMPLE 4

2-N,N-diisopropylamino-1,3,2-dithiaphospholane

A. Into a solution of 20 mmoles of anhydrous pyridine in benzene (25 mL) was added at 0°–5° C., dropwise, with stirring, simultaneously: 10 mmoles of 1,2-ethanedithiol and 10 mmoles of phosphorus trichloride. The reaction mixture was then stirred at room temperature for 1 h. Pyridine hydrochloride was filtered off and the filtrate was evaporated under reduced pressure. The residue was distilled at 14 mmHg to give 1.15 g (73%) 2-chloro-1,3,2-dithiaphospholane as a colorless liquid, b.p. 110° C. $^{31}$P NMR: δ170.7 ppm ($C_6D_6$).

B. Into a solution of 2-chloro-1,3,2-dithiaphospholane (10 mmole) in benzene (25 mL) was added, dropwise at 0°–5° C., with stirring, N,N-diisopropylamine (20 mmole). The reaction mixture was then stirred at room temperature for 1 h. Diisopropylamine hydrochloride was filtered off and the filtrate was evaporated under reduced pressure. The residue was distilled at 0.6 mmHg yielding 1.4 g (63%) of 2-N,N-diisopropylamino-1,3,2-dithiaphospholane in the form of a colorless liquid, b.p. 110° C. $^{31}$P NMR: δ93.9 ppm ($CD_3CN$)

EXAMPLE 5

N₆-isopropoxyacetyl-5'-O-(4,4'-dimethoxytriphenylmethyl)-2-deoxyadenosine-3'-O-[1,3,2-oxathiaphospholane-2-sulfide]

1 mmole N₆-isopropoxyacetyl-5'-O-DMT-2'-deoxyadenosine and 1 mmole 1-H-tetrazole were dried under vacuum at 5° C. After dissolving in anhydrous methylene chloride (3 mL) 2-diisopropylamino-1,3,2-oxathiaphospholane (1.1 mmole) was added with stirring. Stirring was continued for 1 h at ambient temperature and then 10 mmole of elemental sulfur was added and stirred overnight. The reaction mixture was concentrated to dryness and purified on a silica gel column. Yield: 90% $^{31}$P NMR: $\delta$103.63; $\delta$103.58 ppm ($C_6D_6$), 85% $H_3PO_4$ as an external standard.

EXAMPLE 6

$N_4$-isopropoxyacetyl-5'-O-DMT-2'-deoxycytidine-3'-O-[1,3,2-oxathiaphosholane-2-sulfide]

The same procedure was followed as in Example 5, with the exception that $N_4$-isopropoxyacetyl-5'-O-DMT-2'-deoxycytidine was used as starting material. Yield: 87–88%. $^{31}$P NMR: $\delta$104.38; $\delta$104.36 ppm ($C_6D_6$), 85% $H_3PO_4$ as an external standard.

EXAMPLE 7

$N_2$-isopropoxyacetyl-5'-O-DMT-2'-deoxyguanosine-3'-O-[1,3,2-oxathiaphospholane-2-sulfide]

The same procedure was followed as in Example 5, with the exception that $N_2$-isopropoxyacetyl-5'-O-DMT-2'-deoxyguanosine was used as starting material. Yield: 72%. $^{31}$P NMR: $\delta$103.66; $\delta$103.58 ppm ($C_6D_6$), 85% $H_3PO_4$ as an external standard.

EXAMPLE 8

5'-O-DMT-2'-deoxythymidine-3'-O-[1,3,2-oxathiaphospholane-2-sulfide]

The same procedure was followed as in Example 5, with the exception that 5'-O-DMT-2'-deoxythymidine was used as starting material. Yield: 92%. $^{31}$P NMR: $\delta$104.14; $\delta$104.12 ppm ($C_6D_6$), 85% $H_3PO_4$ as an external standard.

EXAMPLE 9

Separation of the Stereo-isomers of the Synthons of Examples 5–8

Diastereoisomeric mixtures of the synthons ($A^{ipa}$, $C^{ipa}$, $G^{ipa}$, and T represent the products of Examples 5–8, respectively) were separated on silica gel (Kieselgel 60 H) columns (200×60 mm) as indicated in the table below. 1 g of the product was applied in each case.

EXAMPLE 10

Further Synthesis of Nucleoside-3'-O-[2-thiono-1,3,2-oxathiaphospholane] Synthons Nucleoside synthons were prepared with the exocyclic amines of the base moieties protected as follows: $N_6$-benzoyladenine, $N_4$-benzoylcytosine, and $N_2$-isobutyrylguanine (the corresponding synthons being represented as $A^{bz}$, $C^{bz}$, and $G^{ibu}$, respectively, and the thymidine synthon as T). Each of the four synthons were prepared as follows: The mixture of the respective protected 5'-DMT-O-(2'-deoxyribonucleoside) (10 mmol) and 1H-tetrazole (0.77 g, 11 mmol) was dried under high vacuum for 5 h and then dissolved in dichloromethane (25 mL). Into this solution the product of Example 2 (2.28 g, 11 mmol) was added dropwise over 10 min and the resulting mixture was maintained at room temperature with stirring for 2 h. Elemental sulfur (0.48 g, 15 mmol), previously dried on a vacuum line for several hours, was added in one portion to the reaction mixture which was left overnight with stirring. Unreacted sulfur was filtered off and solvent was evaporated on a rotatory evaporator. The residue was dissolved in chloroform (3 mL) and applied to a silica gel (30 cm×6 cm column, 170 g of 230–400 mesh silica). Elution was performed first with $CHCl_3$ (200 mL) and then with $CHCl_3$:$CH_3OH$ (97:3, v/v). Isolation was monitored by HPTLC of collected fractions. Collected fractions containing the respective products were pooled together and evaporated. After solvent evaporation, all products were obtained as white foamy solids and consisted of mixtures of the respective $S_p$ and $R_p$ diastereoisomers (in yields of 90%, 89%, 85%, and 92% for $A^{bz}$, $C^{bz}$, $G^{ibu}$, and T, respectively).

The pure diastereoisomers in all cases were obtained by procedures similar to that which follows for $C^{bz}$. 1 g of the $C^{bz}$ product was dissolved in ethyl acetate (4 mL) and loaded onto a column (30 cm×6 cm) of silicagel 60H (200 g, Merck, Art. No. 7736). Diastereoisomers were eluted with ethyl acetate and fractions of 15 mL were collected. Elution of products was followed by means of HPTLC (threefold development in ethyl acetate; detection: HCl spray). Fractions containing separated diastereoisomers (FAST: fractions 61–73, and SLOW: fractions 87–98) were pooled together, respectively, concentrated to dryness under reduced pressure, and the residue was characterized by means of $^{31}$P NMR and HPLC (using Lichrospher Si100, 5 μm (30 cm×7.8 mm), with ethyl acetate as an eluent-flow rate 3 mL/min). For the FAST diastereoisomer: 250 mg recovery (yield 25%), $^{31}$P NMR (in $C_6D_6$, $H_3PO_4$ as external standard): $\delta$104.31 ppm (benzene) 100% diastere-

| | | | Faster Eluted Isomer | | Slower Eluted Isomer | |
|---|---|---|---|---|---|---|
| Synthon | Eluent | Ratio | Amt. | $^{31}$P NMR | Amt. | $^{31}$P NMR |
| $A^{ipa}$ | ethyl acetate: heptane | 2:1 | 300 mg | 103.58 | 250 mg | 103.63 |
| $C^{ipa}$ | ethyl acetate: methylene chloride | 1:1 | 350 mg | 104.36 | 200 mg | 104.38 |
| $G^{ipa}$ | ethyl acetate: methylene chloride: methanol | 2:1:0.2 | 230 mg | 103.50 | 150 mg | 103.66 |
| T | ethyl acetate: heptane | 2:1 | 350 mg | 104.12 | 200 mg | 104.14 | oisomeric purity. For the SLOW diastereoisomer: 180 mg recovery (yield 18%), $^{31}$P NMR: δ104.26 ppm (benzene) 100% d.p. Fractions 74–86 were recycled for repeated isolations of the isomers. Data on the isolated synthons is summarized in the table below:

| Synthon | Faster Eluted Isomer | | Slower Eluted Isomer | |
|---|---|---|---|---|
| | $^{31}$P NMR | $R_f$ | $^{31}$P NMR | $R_f$ |
| $A^{bz}$ | 103.23 | 0.34 | 103.18 | 0.31 |
| $C^{bz}$ | 104.31 | 0.27 | 104.26 | 0.22 |
| $G^{ibu}$ | 104.52 | 0.22 | 104.17 | 0.20 |
| T | 104.27 | 0.59 | 104.23 | 0.57 |

EXAMPLE 11

5'-O-DMT-thymidine-3'-O-[2-thiono-4,4-dimethyl-1,3,2-oxathiaphospholane 1 mmol of 5'-O-DMT-thymidine and 1 mmol of 1H-tetrazole were dried under vacuum for 3 h. 4 mL of $CH_2Cl_2$ were added and then the resulting solution was mixed with 1 mmol of 2-N,N-diisopropylamino-4,4-dimethyl-1,3,2-oxathiaphospholane. Phosphitylation was followed by means of TLC ($CHCl_3$: MeOH at 9:1). After disappearance of the phosphitylating reagent, to the reaction mixture 1 mmol of elemental sulfur was added and the reaction was stirred for 2 h at room temperature. Products were purified on a silicagel column using $CHCl_3$. Yield: 68%, $R_f$ (TLC) 0.74 ($CHCl_3$: MeOH at 9:1). $^{31}$P NMR: 108.08; 107.80 ppm ($CD_3CN$).

EXAMPLE 12

Nucleoside-5'-O-DMT-3'-O-[2-thiono-1,3,2-dithiaphospholane] Synthons

The product of Example 4 was reacted as described in Example 11 with 5'-DMT-protected nucleosides (exocyclic amines being protected as in Example 10) to give the 2-thiono-1,3,2-dithiaphospholane synthons. It was found that the effectiveness of the sulfurization was enhanced by the presence of trace amounts of pyridine. The results are given below:

| Synthon | Yield | $R_f$ (TLC) | $^{31}$P NMR ppm |
|---|---|---|---|
| $A^{bz}$ | 62.4% | 0.80 | 123.95 ($CD_3CN$) |
| $C^{bz}$ | 81.4% | 0.74 | 124.70 ($CD_3CN$) |
| $G^{ibu}$ | 50.4% | 0.61 | 124.96 ($CD_3CN$) |
| T | 74.4% | 0.65 | 121.93 ($C_6D_6$) |

EXAMPLE 13

5'-O-DMT-thymidine-3'-O-[2-seleno-1,3,2-oxathiaphospholane]

5'-O-DMT-thymidine was reacted with 2-N,N-diisopropylamino-1,3,2-oxathiaphospholane and elemental selenium under conditions analogous to those of Example 11. Yield 80%, $^{31}$P NMR: 99.05, 98.90 ppm, ($CHCl_3$), $J_{PSe}$ 952.16 Hz, $R_f$ 0.77 ($CHCl_3$:MeOH at 9:1).

EXAMPLE 14

Synthesis of 5'-O-DMT-nucleosides Bound to Solid Phase Support Via Sarcosinyl Linker A. Long chain alkylamine CPG (LCA-CPG, Sigma, Cat. No. L-8638, 500 A, 80–130 mesh, 2 g) and N-Fmoc-sarcosine (Bachem Bioscience, Inc., Prod. No. B-1720, 0.5 g, 1.6 mmol) were mixed together and dried under high vacuum for 3 h. Dry dimethylformamide (5 mL), pyridine (0.5 mL) and dicyclohexylcarbodiimide (0.5 g, 2.4 mmol) were added and the whole mixture placed in a tightly closes vial (7.4 mL) was gently shaken for 12 h. A suspension of the solid phase support was transferred into sintered glass funnel, solvent removed by suction and the support was washed three times with methanol/acetonitrile/pyridine (1:1:1, v/v/v, 3×20 mL). Residual solvents were removed under high vacuum and the N-Fmoc-sarcosinylated LCA-CPG was suspended in a 10% solution of piperidine in pyridine (v/v, 10 mL) for 0.5 h to remove the Fmoc protecting group. The N-sarcosinylated LCA-CPG was filtered off and washed with methanol/acetonitrile/pyridine (1:1:1, v/v/v, 3×20 mL) and subsequently dried under high vacuum for 5 h.

B. The product obtained according to A (0.5 g) was separately mixed with the respective 3'-O-succinylated 5'-O-DMT-$dA^{bz}$, -$dG^{ibu}$, -$dC^{bz}$, and -dT, and the mixtures were dried under high vacuum for 2 h, after which DMF (2 mL), pyridine (0.2 mL), and DCC (50 mg) were added and the resulting mixtures were moderately shaken at room temperature in tightly closed vials for 12 h. A suspension of the solid support from each mixture was separately transferred to a sintered glass funnel, washed three times with methanol/acetonitrile/pyridine (1:1:1, v/v/v, 3×20 mL), and finally with acetonitrile (3×10 mL). After drying with a flow of dry nitrogen, the supports were treated with an acylating reagent (N-methylimidazole/THF, 1 mL, Applied Biosystems, Inc. Cat. No. 400785, and acetic anhydride/lutidine/THF, 1 mL, Applied Biosystems, Inc. Cat. No. 400607) for 15 min. After a thorough wash with methanol/acetonitrile/pyridine (1:1:1, v/v/v, 3×10 mL) and acetonitrile (3×10 mL), the resulting solid phase supports were dried under high vacuum. Loading of the supports with the respective nucleoside as determined by trityl assay were as follows: CPG-sarcosinyl-$dA^{bz}$: 42.7 μmol/g; CPG-sarcosinyl-$dG^{ibu}$: 46.7 μmol/g; CPG-sarcosinyl-$dC^{bz}$: 31.6 μmol/g; and CPG-sarcosinyl-dT: 35.0 μmol/g.

EXAMPLE 15

2'-deoxyadenyyl-(3',5')-2'-deoxyadenosine phosphorothioate ($R_p$ isomer)

A. Through a column (volume 110 μL), secured with a filter at each end, and containing 1 μmol of $N_6$-isopropoxyacetyl-5'-O-DMT-2'-deoxyadenosine (Uznanski et al, Nucleic Acids Research, Vol. 17, pgs. 4863–4868 (1989)) attached to a solid support, 5 mL of 2% dichloroacetic acid in methylene chloride was passed for 1 minute, then the support was washed with 15 mL of acetonitrile and dried under high vacuum.

B. Into the column prepared as described above, 110 μL of the solution containing 30 μmol of $N_6$-isopropoxyacetyl-5'-O-DMT-2'-deoxyadenosine-3'-O-1,3,2-oxathiaphospholane-2-sulfide (slower eluting diastereoisomer) and 300 μmol of 1,8-diazabicyclo [5.4.0]-undec-7-ene (DBU) was introduced. The reaction was continued for 20 minutes at 18°–24° C. The column was washed with 10 mL of acetonitrile, and then 5 mL of 2% dichloroacetic acid in methylene chloride was passed in order to deprotect the 5'-hydroxyl function.

C. After a thorough wash with acetonitrile, 1 mL of 25% ammonia solution was slowly passed through the column for 1 h in order to cleave the dimer from the solid support and to deprotect the exocyclic amino functions. The product was purified by means of HPLC (PRP1 Hamilton column, 30×7 mm) using a gradient of 5–20% acetonitrile-water, 0.1M triethylammonium bicarbonate (TEAB), flow rate 3 mL/min.

EXAMPLE 16

($R_pR_pR_pR_p$ $R_pR_p$ $R_pR_p$)-Octathymidyl phosphorothioic acid

The synthesis was performed as described in Example 14, except that 5'-O-DMT-thymidine-3'-O-1,3,2-oxathiaphospholane synthons (slower eluting diastereoisomers) were used in 7 coupling cycles. The product was washed, cleaved and deprotected, and purified as described in Example 14.

The product was assayed by snake venom phosphodiesterase (svPDE)(Crotalus adamanteus), which is known to hydrolyze $R_p$ isomers of phosphorothioates, and by nuclease P1 (Penicillium citrinum), which is known to hydrolyze $S_p$ isomers of phosphorothioates. Buffer I was prepared for the svPDE: 100 mM Tris HCl pH 8.5 and 15 mM $MgCl_2$. Buffer II was prepared for nuclease P1: 100 mM Tris HCl pH 7.21 mM $ZnCl_2$. For the svPDE assay, 1 optical density unit of the octathymidyl phosphorothioic acid product was added to 20 μg of svPDE in 500 μL of Buffer I and incubated for 24 h at 37° C. HPLC analysis as described in Example 14 showed that the product was completely hydrolyzed to thymidine-5'-phosphorothioate. For the nuclease P1 assay, 1 optical density unit of the octathymidyl phosphorothioic acid product was added to 10 μg of svPDE in 500 μL of Buffer II and incubated for 24 h at 37° C. HPLC analysis as described in Example 14 showed that the product was completely resistant to hydrolysis by the enzyme.

EXAMPLE 17

($S_pS_pS_pS_pS_pS_pS_pS_p$)-Octathymidyl phosphorothioic acid

The completely $S_p$-chiral octathymidyl phosphorothioic acid was synthesized as in Example 15, except that the faster eluting ($S_p$) diastereoisomer of 5'-O-DMT-thymidine- 3'-O-1,3,2oxathiaphospholane-2-sulfide was used as the synthon. The product was assayed svPDE and nuclease P1 as in Example 15 and was found to be completely resistant to svPDE and to be completely hydrolyzed by nuclease P1.

EXAMPLE 18

Dithymidyl-(3',5')phosphorodithioate

A. In solution.

The mixture of 5'-O-DMT-thymidine-3'-O-[2-thiono-1,3,2-dithiaphospholane] (0.3 mmol) and 3'-O-acetyl thymidine (0.3 mmol) was dried under vacuum for 3 h, then dissolved in 3 mL of anhydrous $CH_3CN$. To this solution 0.33 mmol of DBU was added and this mixture was maintained, with stirring, for 3 h at ambient temperature. $^{31}P$ NMR examination showed presence of 70% of 3'-O-5'-O-protected dithymidyl-(3',5')-phosphorodithioate (δ116.7 ppm), 2% of unreacted synthon, and 28% of side products (δ71.8 and δ72.2 ppm). Evaporation of solvent left solid which was dissolved in 3 mL of 80% $CH_3COOH$. After 2 h acetic acid was removed under reduced pressure and residue was redissolved in 5 mL of 25% $NH_4OH$. This solution was incubated at 55° C. for 15 h. After concentration and dissolution in 5 mL of water, solid particles were filtered off and filtrate was introduced into a column filled with DEAE-Sephadex A-25. Product was eluted with TEAB, gradient 0.05-1M. UV-absorbing fraction was collected and concentrated. $^{31}P$ NMR ($D_2O$) showed the presence of product, δ113.8 ppm, purity >95%, Yield from UV absorption profile, 46.6%. Further analysis by FAB-MS confirmed product as dithymidyl-(3',5') -phosphorodithioate.

B. On solid support.

1 μmol of CPG-T in a column (Applied Biosystems, Inc.) was detritylated and 10 μmol of 5'-O-DMT-thymidine-3'-O-[2-thiono-1,3,2-dithiaphosphalane] (dried under vacuum) diluted with 140 μL of $CH_3CN$ was introduced to the column together with 10 μmol of DBU in 15 μL of $CH_3CN$. After 10 minutes (with occasional shaking), the column was washed with $CH_3CN$, detritylated, and deprotected and cleaved using standard procedures. HPLC analysis (ODS Hypersil; linear gradient 5→20% $CH_3CN$ in 0.1M TEAB, 20 min, R.T. 12.3 min.) showed product consisted of dithymidyl phosphorodithioic acid contaminated with 8% thymidine.

EXAMPLE 19

Dithymidyl-(3', 5')-phosphoroselenoate.

A. In solution.

0.1 mmol of the product from Example 13 in 0.5 mL $CH_3CN$ was added to the mixture of 0.1 mmol 3'-O-methoxyacetyl thymidine and 0.15 mmol DBU. After 10 min $^{31}P$ NMR examination showed the presence of about 80% of 3',5'-protected dithymidyl-(3',5')-phosphoroselenoate (δ49.7 and δ49.5 ppm) and 20% of unidentified side products (δ59.7 and δ59.6 ppm).

B. On a solid support.

1 μmol of CPG-T in a column (Applied Biosystems, Inc.) was detritylated and 10 μmol of 5'-O-DMT-thymidine-3'-O-[2-seleno-1,3,2-oxathiaphospholane] diluted with 50 μL $CH_3CN$ was introduced to the column together with 20 μmol of DBU in 100 μL of pyridine. After 10 min, the column was washed with acetonitrile, detritylated, and the product was cleaved from the support. HPLC analysis (ODS Hypersil, linear gradient 5→20% $CH_3CN$ in 0.1M TEAB over 20 min. R.T. of 8.87 and 9.54. Yield: 85% (via HPLC).

EXAMPLE 20

Control of Stereospecificity under Conditions of Automated Solid Phase Synthesis An Applied Biosystems, Inc. (Foster City, Calif., USA) model 380B automated DNA synthesizer was employed using the manufacturer's columns (1 μmol scale). The maanufacturer's program used routinely for the synthesis of oligonucleotides via the 2-cyanoethylphosphoramidite method was modified according to the protocol presented in the following table:

| Chemical steps for one synthesis cycle | | | |
|---|---|---|---|
| Step | Reagent or Solvent | Purpose | Time (min) |
| 1 | a) Dichloroacetic acid in $CH_2Cl_2$ (2:98, v/v) | 2 mL DETRITYLATION | 1.5 |
|   | b) Acetonitrile | 5 mL WASH | 2 |
| 2 | a) Activated nucleotide in acetonitrile* | COUPLING | 10 |
|   | b) Acetonitrile | 5 mL WASH | 2 |
| 3 | a) Acetic anhydride/lutidine in THF (10:10:80, v/v/v) | 1 mL CAPPING | 1 |
|   | N-methylimidazole in THF (16:84, v/v) | 1 mL | |
|   | b) Acetonitrile | 5 mL WASH | 1 |

*For 1 μmol synthesis scale 2 M DBU in pyridine (150 μL), and 0.1 M 5'-O-DMT-deoxynucleoside-3'-O-[2-thiono-1,3,2-oxathiaphospholane] (of Example 10) (50 μL) in acetonitrile was used.

Reservoirs 1–4 of the DNA synthesizer were filled with solutions of pure diastereoisomers (Example 10) in acetonitrile (0.1M), and reservoir 9 (usually containing the 1H-tetrazole activator) was filled with 2M DBU in pyridine. In each case, at the completion of synthesis, acidic detritylation was followed by ammonia cleavage and base deprotection. Products (dimers) were analyzed and purified by reverse phase HPLC using an ODS Hypersil (5 μm) column (30 cm×4.6 mm) that was eluted with the linear gradient of acetonitrile: 5→20% $CN_3CN$/0.1 mol TEAB; 0.75%/min; flow rate 1.5 mL/min. Results are summarized in the table below, HPLC profiles are given in Stec et al, Nucleic Acids Research, Vol. 19, pgs. 5883–5888 (1991):

| | Stereospecificities of the formation of dinucleotide-(3',5')-phosphorothioates | | |
|---|---|---|---|
| Synthon (a) | Diastereomeric purity (b) | Product | Diastereomeric purity (c) |
| T | FAST 100% | $[S_p]$-d(TT) | 99.0% |
| T | SLOW 100% | $[R_p]$-d(TT) | 100.0% |
| $A^{bz}$ | FAST 100% | $[S_p]$-d(AA) | 99.4% |
| $A^{bz}$ | SLOW 100% | $[R_p]$-d(AA) | 99.5% |
| $C^{bz}$ | FAST 100% | $[S_p]$-d(CC) | 99.3% |
| $C^{bz}$ | FAST 95% (d) | $[S_p]$-d(CC) | 95.0% |
| $C^{bz}$ | SLOW 100% | $[R_p]$-d(CC) | 99.5% |
| $C^{bz}$ | SLOW 95% (d) | $[R_p]$-d(CC) | 95.0% |
| $G^{ibu}$ | FAST 100% | $[S_p]$-d(GG) | 99.3% |
| $G^{ibu}$ | SLOW 100% | $[R_p]$-d(GG) | 98.0% |

(a) Same nomenclature as in Example 10.
(b) All the diastereoisomeric synthons were identified via HPLC by coinjections with genuine samples prepared according to Stec at al, J. Amer. Chem. Soc., Vol. 106, pgs. 6077–6079 (1984).
(c) Via HPLC.
(d) Prepared by mixing separated diastereoisomers.

As can be seen from the above data, the SLOW eluting diastereoisomers are always giving a dinucleotide product in the $R_p$ configuration, while the FAST eluting diastereoisomers are always giving a dinucleotide product in the $S_p$ configuration.

EXAMPLE 21

Control of Stereospecificity under Conditions of Automated Solid Phase Synthesis Using Nucleosides Bound to Solid Phase Support Via Sarcosinyl Linker The procedures of Example 20 are followed, except that in place of the manufacturer's columns, columns are provided that are filled with 5'-DMT-nucleosides bound to a solid phase support via a sarcosinyl linker as described in Example 14.

EXAMPLE 22

$(R_pR_pR_pR_pR_p)$-penta-(2'-O-deoxycytidine phosphorothioate)

A $(R_pR_pR_pR_pR_p)$-penta-(2'-O-deoxycytidine phosphorothioate) was synthesized with an automated DNA synthesizer as described in Example 19 using the CPG-sarcosinyl-$dC^{bz}$ solid phase support as described in Example 20. A solution of the SLOW eluting synthon of Example 10 (100 mg) in acetonitrile (1.2 mL) was employed. Tritylated and detritylated products were isolated by two-step reverse phase HPLC. Analysis of both the tritylated and detritylated products by HPLC (same column as in Example 19) gave rise to single peaks (flow rate 1.5 mL/min). For tritylated compound: r.t. 20.40 min (5–30% $CH_3CN$/0.1M TEAB, t=20 min, exponent 0.25). For detritylated product: r.t. 11.80, 5–20% $CH_3CN$/0.1M TEAB, 0.75%/min). Preparative yield: 14%. Enzymatic analysis as described above showed the product to be of all-$R_p$ form.

EXAMPLE 23

$(S_pS_pS_pS_p)$-penta-(2'-O-deoxycytidine phosphorothioate)

A $(S_pS_pS_pS_pS_pS_p)$-penta-(2'-O-deoxycytidine phosphorothioate) was prepared as described in Example 21, except that the FAST eluting synthon was employed. With the same analysis as in Example 21, the tritylated compound had a r.t. of 20.7 min, and the detritylated product had a r.t. of 12.00 min. Preparative yield: 15%. Enzymatic analysis as described above showed the product to be of all-$S_p$ form.

EXAMPLE 24

Synthesis of P-chiral Antisense Compound

All-$R_p$ and all-$S_p$ forms of the 28-mer antisense oligonucleotide phosphorothioate, 5'-TCGTCGCTGTCTCCGCTTCTFCCTGCCA, are synthesized with an automated DNA synthesizer as described by Examples 19 and 20 using the SLOW and FAST eluting synthons of Example 10, respectively.

We claim:

1. A method of synthesizing a P-chiral oligonucleotide phosphorothioate of a predetermined length, the P-chiral oligonucleotide comprising a sequence of nucleosides or nucleoside analogs and phosphorothioate or phosphodiester linkages, the phosphorothioate linkages being $R_p$ chiral or $S_p$ chiral, the method comprising the steps of:

(a) providing a first nucleoside or nucleoside analog attached to a solid phase support, the first nucleoside or nucleoside analog having a protected hydroxyl;

(b) deprotecting the protected hydroxyl to form a free hydroxyl;

(c) reacting with the free hydroxyl a synthon selected from the group defined by the formula:

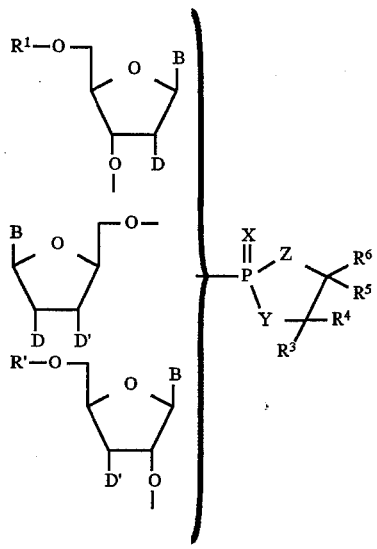

wherein:

$R^I$ is a hydroxyl protecting group;

B is a purine or a pyrimidine;

D is hydrogen, halogen, hydroxyl, or —OR', wherein R' is alkyl having from 1 to 3 carbon atoms or a 2'-hydroxyl protecting group;

D' is hydrogen, hydroxyl, or —OR" such that R" is a 3'-hydroxyl protecting group;

X is sulfur, Y is oxygen, and Z is sulfur; and $R^3$, $R^4$, $R^5$, and $R^6$ are separately hydrogen or alkyl having from 1 to 4 carbon atoms or are separately or together with the carbon atoms to which they are attached aryl or alkyl-substituted aryl having from 6 to 12 carbon atoms; and (d) repeating steps (b) and (c) until the predetermined length of the P-chiral oligonucleotide phosphorothioate is achieved.

2. The method of claim 1 wherein said step of reacting includes reacting in the presence of a catalytic base.

3. The method of claim 2 further including the step of capping unreacted free hydroxyls after said step (c).

4. The method of claim 3 wherein said synthon is selected from the group defined by the formula:

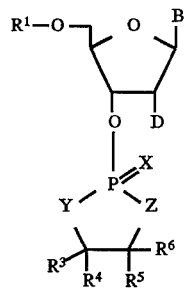

5. The method of claim 4 wherein $R^3$, $R^4$, $R^5$, and $R^6$ are separately hydrogen or methyl.

6. The method of claim 5 wherein said predetermined length of said P-chiral oligonucleotide phosphorothioate is in the range of 12 to 60 nucleosides or nucleoside analogs.

7. The method of claim 6 wherein said catalytic base is 1,8-diazabicyclo[5.4.0]undec-7-ene.

* * * * *